United States Patent [19]

Harris et al.

[11] Patent Number: 5,348,735
[45] Date of Patent: Sep. 20, 1994

[54] LIQUID CRYSTAL DEODORANT

[75] Inventors: Dennis Harris, Scottsdale; Ronald General, Phoenix, both of Ariz.

[73] Assignee: GHS Products, Inc., Scottsdale, Ariz.

[21] Appl. No.: 76,422

[22] Filed: Jun. 14, 1993

[51] Int. Cl.$^5$ .......................... A61K 7/32; A61K 7/38; A61K 33/06
[52] U.S. Cl. ..................... 424/65; 424/401; 424/698; 514/848; 514/946
[58] Field of Search .............. 424/65, 401, 76.8, 698; 514/946, 848

[56] References Cited

U.S. PATENT DOCUMENTS 4,879,116 11/1989 Fox et al. .......................... 514/848

OTHER PUBLICATIONS

Sagarin, Cosmetics Science and Technology, 1957, pp. 368, 369, 455, 717 to 720, 764 to 767.
Pharmaceutical Formulas, 1946, 10th edition, vol. II, pp. 109, 150–153, 304 and 305.
Bennett, The Cosmetic Formulary, 1941, pp. 54 to 56 and 63.
Harry, The Principles and Practice of Modern Cosmetics, 1962, vol. One, pp. 471 to 481.

*Primary Examiner*—Dale R. Ore
*Attorney, Agent, or Firm*—LaValle D. Ptak

[57] ABSTRACT

A liquid crystal deodorant is produced by dissolving a powdered crystalline double sulfate of aluminum (alum) in a saturated solution of water, or a combination of water and alcohol, preferably denatured ethanol. The deodorant then is applied in any suitable fashion to provide odor control, particularly for underarm and foot odor control purposes.

4 Claims, No Drawings

LIQUID CRYSTAL DEODORANT

BACKGROUND

A variety of different products have been developed for use as body deodorants, particularly for underarms and feet. Personal body deodorants are sold in several different forms. For example, underarm and foot deodorants/anti-perspirants may be sold as dry powders, liquid roll-on deodorants, wax-like stick deodorants, and spray deodorants. In whatever form such deodorant-/antiperspirants are sold, a common widely used primary ingredient: is aluminum chlorohydrate. This material is dissolved or placed in a suitable carrier. In the case of liquid and spray deodorants, a primary component of the carrier is an alcohol such as propylene glycol or the like. The aluminum chlorohydrate serves as a drying agent to reduce perspiration; and odor control also is provided by other ingredients, such as cyclomethicone.

Recently, a different type of natural deodorant has been marketed. This deodorant comprises a solid crystalline double sulfate of aluminum, such as potassium aluminum sulfate or ammonium aluminum sulfate. These solid crystals are wetted on the surface, and then are rubbed over the area to which the deodorant is to be applied. A small amount of the crystal dissolves in the water on its surface, and transfers to the body portions over which the crystal is rubbed. It has been found that such crystalline double sulfates of aluminum (alum) provide good odor and wetness control for long periods of time. A disadvantage to such solid crystalline alum products is that they are somewhat more difficult to apply than standard deodorants (because of the wetting step). Also, if the crystal is dropped, it is subject to shattering or breaking.

It is desirable to provide a deodorant which has the advantages of crystalline double sulfates of aluminum, and which is capable of application by means of a spray or roll-on delivery system.

SUMMARY OF THE INVENTION

It is an object of this invention to provide an improved deodorant product.

It is another object of this invention to provide an improved crystalline alum deodorant product.

It is an additional object of this invention to provide an improved personal deodorant using dissolved crystalline alum.

It is a further object of this invention to provide an improved liquid crystal deodorant using potassium aluminum sulfate or ammonium aluminum sulfate as the primary active ingredient.

In accordance with a preferred embodiment of this invention, a liquid crystal deodorant is made by dissolving powdered crystalline alum in a solution which comprises water as a primary liquid component. In more specific embodiments, the liquid component also includes alcohol in the form of denatured ethanol or propylene glycol, or a combination of both.

DETAILED DESCRIPTION

In accordance with a preferred embodiment of this invention, a personal body deodorant is made of crystalline double sulfate of aluminum (alum), in which the crystals first are ground to a powder. The powder then is dissolved in a solution comprising water or water and alcohol. The solution then may be delivered as a personal body deodorant by means of a conventional spray or roll-on delivery system. Two types of alum (crystalline double sulfates of aluminum) may be used, i.e. potassium alum (potassium aluminum sulfate) and ammonium alum (ammonium aluminum sulfate). Actual test results for both types are similar.

In formulating various solutions suitable for spray or roll-on application, powdered crystal, comprising nearly one hundred percent of potassium aluminum sulfate or ammonium aluminum sulfate, with only trace amounts of other materials, comprises the active odor control ingredient.

The following nine examples, all using potassium alum as the powdered crystal, dissolved in varying amounts in different liquid carriers, are provided, showing actual test results.

EXAMPLE 1

| 1. | COMPOSITION | RANGES |
|---|---|---|
|  | Powdered crystal | 2.5–14.0 grams |
|  | Distilled water | 100 ml |

Methodology

Powdered crystal was mixed with distilled water. Used cold, room temperature and hot. Filtered before bottling.

Results a) Chemical—large crystals formed with all compositions exceeding 4.5 gm/100 ml. The supernatant liquid was clear.

b) Clinical—2.5–3.5 gm/100 ml provided good odor control with sedentary activities, but breakthrough occurred frequently with moderate or greater activity. 4.5 gm/100 ml provided good odor control with most levels of activity, but breakthrough occurred periodically with heavier activity. Drying time was poor with all samples, and dripping and messiness was constant. Excellent odor control on feet and perineal area with no irritation.

Subjects

A total of 32 subjects were tested using sniff test, 4 in each range of 2.5, 3.0, 3.5, 4.0, 4.5, 5.0, 7.0 and 14 gm/100 ml.

EXAMPLE 2

| 2. | COMPOSITION | RANGES |
|---|---|---|
|  | Powdered crystal | 2.5–7.0 gm/100 ml |
|  | Denatured alcohol | 20%–50% |
|  | Distilled water | 50%–80% |

Methodology

Dissolved powdered crystal in distilled water. Added denatured alcohol while stirring gently. Entire range of temperatures used in Example 1. Filtered prior to adding denatured ethanol.

Results a) Chemical—formation of large crystals occurred with all formulae. Supernatant liquid was clear.

b) Clinical

1) Underarm deodorant—mixtures of less than 4.5 gm/100 ml resulted in poor odor control with moderate to strenuous activity. Mixtures containing less than 4.5 gm/100 ml produced excellent solubility of the powdered crystal. An offensive odor was present with all formulae, and that odor persisted for several minutes before dissipating. Odor control (by the sniff nest) was good with all mixtures using 4.5 gm/100 ml at low to moderate levels of activity, but breakthrough occurred frequently with strenuous activity of heavy sweating. Mixtures containing concentrations below 4.5 gm/100 ml produced poor odor control at all but low levels of activity. Mild skin irritation occurred with all concentrations of denatured alcohol above 25%. Drying time was poor at concentrations less than 30% denatured ethanol and fair to good above that level. Dripping and messiness was moderate.

2) Foot deodorant—mixtures containing 3.5 gm/100 ml or more were effective in producing good odor control by the sniff test. Less than 3.5 gm/100 ml resulted in poor odor control. The spray produced a cooling sensation with concentrations of 25% or more of denatured ethanol. No skin irritation occurred. The spray still produced dripping and poor drying time with concentrations of less than 30% denatured ethanol, but these performance characteristics were acceptable when the spray was only applied to the feet.

Subjects

Three subjects tested each of the following concentrations:
a) 2.5 gm/100 ml with 20%, 25%, 30%, 40% and 50% denatured ethanol.
b) 3 5 gm/100 ml with 20%, 25%, 30%, 40% and 50% denatured ethanol.
c) 4.5 gm/100 ml with 20%, 25%, 30%, 40% and 50% denatured ethanol.
d) 5.5 gm/100 ml with 20%, 25%, 30%, 40% and 50% denatured ethanol.
e) 7 0 gm/100 ml with 20%, 25%, 30%, 40% and 50% denatured ethanol.

Therefore, a total of 75 test subjects, many of whom were utilized for several formulations, took part in the evaluations.

EXAMPLE 3

| COMPOSITION | RANGES |
| --- | --- |
| Powdered crystal | 2.5–5.5 gm/100 ml |
| Absolute ethanol | 15%–50% |
| Distilled water | 50%–85% |

Methodology

Powdered crystal was dissolved in distilled water, filtered, and gently mixed with absolute ethanol using gentle stirring. Entire range of temperature used in Example 1.

Results a) Chemical—all formulae produced large crystals, but the supernatant liquid was clear.
b) Clinical
  1) Underarm deodorant—same as Example 2(b) (1) with the following exceptions:
    A) A non-offensive mild alcohol odor was present immediately after application, but cleared completely after less than one (1) minute. No skin irritation occurred.
  2) Foot deodorant—same as Example 2(b) (2) with the following exceptions:
    A) While a moderate cooling sensation was still present at the time of application, the sensation was less pronounced and shorter in duration.

Subjects

Three subjects tested each of the following concentrations:
a) 2.5 gm/100 ml with 15%, 20%, 25%, 30%, 40% and 50% absolute ethanol.
b) 3.5 gm/100 ml with 15%, 20%, 25%, 30%, 40% and 50% absolute ethanol.
c) 4.5 gm/100 ml with 15%, 20%, 25%, 30%, 40% and 50% absolute ethanol.
d) 5.5 gm/100 ml with 15%, 20%, 25%, 30%, 40% and 50% absolute ethanol.

Therefore, a total of 144 tests were performed.

EXAMPLE 4

| 4. | COMPOSITION | RANGES |
| --- | --- | --- |
| | Powdered crystal | 2.5–5.5 gm/100 ml |
| | Propylene glycol | 3%–10% |
| | Absolute ethanol | 10%–50% |
| | Distilled water | 40%–87% |

Methodology

Powdered crystal was dissolved in distilled water, then filtered. In a separate reaction, propylene glycol was mixed with absolute ethanol and gently stirred. The resulting mixture was then added to the clear filtrate from the first reaction and gently stirred.

Results a) Chemical—medium crystal formation was noted with all compositions except those containing 5% propylene glycol or less and 40% absolute ethanol or more. The supernatant liquid was clear.
b) Clinical
  1) Underarm deodorant—same as Example 3(b) (1) with the following exceptions:
    A) Mixtures containing more than 5% propylene glycol were excessively sticky, and this sensation of stickiness remained throughout a 24 hour period. Drying time was good for all mixtures containing 40% or more absolute ethanol and 5% or less propylene glycol. Messiness was only mild in those same conditions. Drying time and messiness were unsatisfactory in all other ranges.
  2) Foot deodorant—same as Example 3(b) (2) (A).

Subjects

Three subjects tested each of the following concentrations:
a) 2.5 gm/100 ml with 3% propylene glycol and 10%, 20%, 30%, 40% and 50% absolute ethanol.
b) 3.5 gm/100 ml with 3% propylene glycol and 10%, 20%, 30%, 40% and 50% absolute ethanol.
c) 4.5 gm/100 ml with 3% propylene glycol and 10%, 20%, 30%, 40% and 50% absolute ethanol.

d) 5.5 gm/100 ml with 3% propylene glycol and 10%, 20%, 30%, 40% and 50% absolute ethanol.
e) 2.5 gm/100 ml with 5% propylene glycol and 10%, 20%, 30%, 40% and 50% absolute ethanol.
f) 3.5 gm/100 ml with 5% propylene glycol and 10%, 20%, 30%, 40% and 50% absolute ethanol.
g) 4.5 gm/100 ml with 5% propylene glycol and 10%, 20%, 30%, 40% and 50% absolute ethanol.
h) 5.5 gm/100 ml with 5% propylene glycol and 10%, 20%, 30%, 40% and 50% absolute ethanol.
i) 2.5 gm/100 ml with 7.5% propylene glycol and 10%, 20%, 30%, 40% and 50% absolute ethanol.
j) 3.5 gm/100 ml with 7.5% propylene glycol and 10%, 20%, 30%, 40% and 50% absolute ethanol.
k) 4.5 gm/100 ml with 7.53 propylene glycol and 10%, 20%, 30%, 40% and 50% absolute ethanol.
l) 5.5 gm/100 ml with 7.5% propylene glycol and 10%, 20%, 30%, 40% and 50% absolute ethanol.
m) 2.5 gm/100 ml with 10% propylene glycol and 10%, 20%, 30%, 40% and 50% absolute ethanol.
n) 3.5 gm/100 ml with 10% propylene glycol and 10%, 20%, 30%, 40% and 50% absolute ethanol.
o) 4.5 gm/100 ml with 10% propylene glycol and 10%, 20%, 30%, 40% and 50% absolute ethanol.
p) 5.5 gm/100 ml with 10% propylene glycol and 10%, 20%, 30%, 40% and 50% absolute ethanol.

Therefore, a total of 480 tests were performed.

EXAMPLE 5

| 5. | COMPOSITION | RANGES |
|---|---|---|
| | Powdered crystal | 2.5–5.5 gm/100 ml |
| | Propylene glycol | 3%–10% |
| | Hexachlorophene | .1 gm–.5 mg/100 ml |
| | Absolute ethanol | 10%–50% |
| | Distilled water | 40%–67% |

Methodology

Powdered crystal was dissolved in distilled water, then filtered. In a separate reaction, propylene glycol was mixed with absolute ethanol and gently stirred. Hexachlorophene was then dissolved in the propylene glycol/absolute ethanol mixture. That solution was then added to the clear filtrate from the first reaction. Filtration of the entire mixture was again performed after 48 hours, resulting in a clear filtrate.

Results a) Chemical—mixtures containing 7.5% or more propylene glycol and/or more than 0.2 gm hexachlorophene produced a dense flocculate that remained partially in suspension for at least 1 week. Mixtures with 5% or less propylene glycol and/or 0.2 gm or less hexachlorophene produced a dense white precipitate that quickly settled to the bottom, leaving a clear supernatant liquid.

b) Clinical

1) Underarm deodorant—mixtures containing 4.5 –5.5 gm/100 ml powdered crystal, 40%–50% absolute ethanol, 3%–5% propylene glycol and 0.1–0.2 gm hexachlorophene were judged to be productive of good to excellent odor control by the sniff test in 80–85% of the test subjects, no skin irritation in 95% of the test subjects, mild to no stickiness in 75% of the test subjects, mild to no messiness (indicative of drying time) in 70% of test subjects and better than their present deodorant or antiperspirant in 90% of test subjects. Staining of clothing occurred in only 1 of 44 test subjects. The remaining compositions were unsatisfactory in 1 or more of the above parameters.

2) Foot deodorant—same as Example 3(b) (2) (A).

Subjects

Two subjects tested each of the following concentrations:

a) 2.5 gm/100 ml powdered crystal with 7.5% propylene glycol, 30% absolute ethanol, and 0.1 gm/100 ml, 0.2 gm/100 ml, 0.35 gm/100 ml and 0.5 gm/100 ml hexachlorophene.
b) 3.5 gm/100 ml powdered crystal with 7.5% propylene glycol, 30% absolute ethanol, and 0.1 gm/100 ml, 0.2 gm/100 ml, 0.35 gm/100 ml and 0.5 gm/100 ml hexachlorophene.
c) 4.5 gm/100 ml powdered crystal with 7.5% propylene glycol, 30% absolute ethanol, and 0.1 gm/100 ml, 0.2 gm/100 ml, 0.35 gm/100 ml and 0.5 gm/100 ml hexachlorophene.
d) 5.5 gm/100 ml powdered crystal with 7.5% propylene glycol, 30% absolute ethanol, and 0.1 gm/100 ml, 0.2 gm/100 ml, 0.35 gm/100 ml and 0.5 gm/100 ml hexachlorophene.
e) 2.5 gm/100 ml powdered crystal with 10% propylene glycol, 30% absolute ethanol, and 0.1 gm/100 ml, 0.2 gm/100 ml, 0.35 gm/100 ml and 0.5 gm/100 ml hexachlorophene.
f) 3.5 gm/100 ml powdered crystal with 10% propylene glycol, 30% absolute ethanol, and 0.1 gm/100 ml, 0.2 gm/100 ml, 0.35 gm/100 ml and 0.5 gm/100 ml hexachlorophene.
g) 4.5 gm/100 ml powdered crystal with 10% propylene glycol, 30% absolute ethanol, and 0.1 gm/100 ml, 0.2 gm/100 ml, 0.35 gm/100 ml and 0.5 gm/100 ml hexachlorophene.
h) 5.5 gm/100 ml powdered crystal with 10% propylene glycol, 30% absolute ethanol, and 0.1 gm/100 ml, 0.2 gm/100 ml, 0.35 gm/100 ml and 0.5 gm/100 ml hexachlorophene.
i) 2.5 gm/100 ml powdered crystal with 7.5% propylene glycol, 40% absolute ethanol, and 0.1 gm/100 ml, 0.2 gm/100 ml, 0.35 gm/100 ml and 0.5 gm/100 ml hexachlorophene.
j) 3.5 gm/100 ml powdered crystal with 7.5% propylene glycol, 40% absolute ethanol, and 0.1 gm/100 ml, 0.2 gm/100 ml, 0.35 gm/100 ml and 0.5 gm/100 ml hexachlorophene.
k) 4.5 gm/100 ml powdered crystal with 7.5% propylene glycol, 40% absolute ethanol, and 0 1 gm/100 ml, 0.2 gm/100 ml, 0.35 gm/100 ml and 0 5 gm/100 ml hexachlorophene.
l) 5.5 gm/100 ml powdered crystal with 7.5% propylene glycol, 40% absolute ethanol, and 0 1 gm/100 ml, 0.2 gm/100 ml, 0.35 gm/100 ml and 0 5 gm/100 ml hexachlorophene.
m) 2.5 gm/100 ml powdered crystal with 10% propylene glycol, 40% absolute ethanol, and 0 1 gm/100 ml, 0.2 gm/100 ml, 0.35 gm/100 ml and 0 5 gm/100 ml hexachlorophene.
n) 3.5 gm/100 ml powdered crystal with 10% propylene glycol, 40% absolute ethanol, and 0 1 gm/100 ml, 0.2 gm/100 ml, 0.35 gm/100 ml and 0 5 gm/100 ml hexachlorophene.
o) 4.5 gm/100 ml powdered crystal with 10% propylene glycol, 40% absolute ethanol, and 0 1 gm/100 ml, 0.2 gm/100 ml, 0.35 gm/100 ml and 0 5 gm/100 ml hexachlorophene.
p) 5.5 gm/100 ml powdered crystal with 10% propylene glycol, 40% absolute ethanol, and 0 1 gm/100 ml, 0.2 gm/100 ml, 0.35 gm/100 ml and 0 5 gm/100 ml hexachlorophene.
q) 2.5 gm/100 ml powdered crystal with 7.5% propylene glycol, 50% absolute ethanol, and 0.1 gm/100 ml, 0.2 gm/100 ml, 0.35 gm/100 ml and 0 5 gm/100 ml hexachlorophene.
r) 3.5 gm/100 ml powdered crystal with 7.5% propylene glycol, 50% absolute ethanol, and 0.1 gm/100 ml, 0.2 gm/100 ml, 0.35 gm/100 ml and 0 5 gm/100 ml hexachlorophene.
s) 4.5 gm/100 ml powdered crystal with 7.5% propylene glycol, 50% absolute ethanol, and 0.1 gm/100 ml, 0.2 gm/100 ml, 0.35 gm/100 ml and 0 5 gm/100 ml hexachlorophene.
t) 5.5 gm/100 ml powdered crystal with 7.5% propylene glycol, 50% absolute ethanol, and 0.1 gm/100 ml, 0.2 gm/100 ml, 0.35 gm/100 ml and 0 5 gm/100 ml hexachlorophene.
u) 2.5 gm/100 ml powdered crystal with 10% propylene glycol, 50% absolute ethanol, and 0.1 gm/100 ml, 0.2 gm/100 ml, 0.35 gm/100 ml and 0 5 gm/100 ml hexachlorophene.
v) 3.5 gm/100 ml powdered crystal with 10% propylene glycol, 50% absolute ethanol, and 0.1 gm/100 ml, 0.2 gm/100 ml, 0.35 gm/100 ml and 0 5 gm/100 ml hexachlorophene.
w) 4.5 gm/100 ml powdered crystal with 10% propylene glycol, 50% absolute ethanol, and 0.1 gm/100 ml, 0.2 gm/100 ml, 0.35 gm/100 ml and 0.5 gm/100 ml hexachlorophene.
x) 5.5 gm/100 ml powdered crystal with 10% propylene glycol, 50% absolute ethanol, and 0.1 gm/100 ml, 0.2 gm/100 ml, 0.35 gm/100 ml and 0.5 gm/100 ml hexachlorophene.

Therefore, a total of 384 tests were performed.

Two subjects tested each of the following compositions:
a) 2.5 gm/100 ml powdered crystal with 3% propylene glycol, 30% absolute ethanol, and 0.1 gm/100 ml, 0.2 gm/100 ml, 0.35 gm/100 ml and 0.5 gm/100 ml hexachlorophene.
b) 3.5 gm/100 ml powdered crystal with 3% propylene glycol, 30% absolute ethanol, and 0.1 gm/100 ml, 0.2 gm/100 ml, 0.35 gm/100 ml and 0.5 gm/100 ml hexachlorophene.
c) 4.5 gm/100 ml powdered crystal with 3% propylene glycol, 30% absolute ethanol, and 0.1 gm/100 ml, 0.2 gm/100 ml, 0.35 gm/100 ml and 0.5 gm/100 ml hexachlorophene.
d) 5.5 gm/100 ml powdered crystal with 3% propylene glycol, 30% absolute ethanol, and 0.1 gm/100 ml, 0.2 gm/100 ml, 0.35 gm/100 ml and 0.5 gm/100 ml hexachlorophene.
e) 2.5 gm/100 ml powdered crystal with 5% propylene glycol, 30% absolute ethanol, and 0.1 gm/100 ml, 0 2 gm/100 ml, 0.35 gm/100 ml and 0 5 gm/100 ml hexachlorophene.
f) 3.5 gm/100 ml powdered crystal with 5% propylene glycol, 30% absolute ethanol, and 0.1 gm/100 ml, 0 2 gm/100 ml, 0.35 gm/100 ml and 0 5 gm/100 ml hexachlorophene.
g) 2.5 gm/100 ml powdered crystal with 3% propylene glycol, 40% absolute ethanol, and 0.1 gm/100 ml, 0 2 gm/100 ml, 0.35 gm/100 ml and 0 5 gm/100 ml hexachlorophene.
h) 3.5 gm/100 ml powdered crystal with 3% propylene glycol, 40% absolute ethanol, and 0.1 gm/100 ml, 0 2 gm/100 ml, 0.35 gm/100 ml and 0 5 gm/100 ml hexachlorophene.
i) 2.5 gm/100 ml powdered crystal with 3% propylene glycol, 50% absolute ethanol, and 0.1 gm/100 ml, 0 2 gm/100 ml, 0.35 gm/100 ml and 0 5 gm/100 ml hexachlorophene.
j) 3.5 gm/100 ml powdered crystal with 3% propylene glycol, 50% absolute ethanol, and 0.1 gm/100 ml, 0 2 gm/100 ml, 0.35 gm/100 ml and 0 5 gm/100 ml hexachlorophene.

Therefore, a total of 160 tests were performed.

Three subjects tested each of the following compositions:
a) 5.5 gm/100 ml powdered crystal with 3% propylene glycol, 40% absolute ethanol and 0.35 gm/100 ml and 0.5 gm/100 ml hexachlorophene.
b) Same with 50% absolute ethanol.

Therefore, a total of 24 tests were performed.

Eleven subjects tested each of the following compositions:
a) 4.5 gm/100 ml powdered crystal with 5% propylene glycol, 40% absolute ethanol and 0.1 gm/100 ml and 0.2 gm/100 ml hexachlorophene.
b) 4.5 gm/100 ml powdered crystal with 5% propylene glycol, 50% absolute ethanol and 0.1 gm/100 ml and 0.2 gm/100 ml hexachlorophene.

Therefore, a total of 88 tests were performed.

EXAMPLE 6

| COMPOSITION | RANGES |
| --- | --- |
| Powdered crystal | 4.5–5 gm/100 ml |
| Propylene glycol | 5% to 15% |
| Dimethicone copolyol phosphate | 1% to 2% |
| SD alcohol 40 | 10% to 40% |
| Deionized water | 38.35% to 75.13% |
| Triclosan | .12% to .17% |

Methodology

Powdered crystal was dissolved in deionized water, then filtered. In a separate reaction, propylene glycol was mixed with SD alcohol 40 and gently stirred. Dimethicone copolyol phosphate and Triclosan were then dissolved in the propylene glycol/SD alcohol 40 mixture, and that solution was added to the clear filtrate from the first reaction.

Results a) Chemical—a mixture containing 15.0% propylene glycol and 40% SD alcohol 40 produced a clear solution, with no crystallization or flocculation. Mixtures which included 5% propylene glycol with 40% SD alcohol 40, and 9.2% propylene glycol with 10% SD alcohol 40, respectively, both produced crystallization in the bottle, with the greatest crystallization taking place in the mixture with the least amount of SD alcohol 40.

b) Clinical

1) Underarm deodorant—all mixtures were judged to be productive of good to excellent odor control by the sniff test in all of the test subjects. In a mixture having 10% SD alcohol 40 and 9.5% propylene glycol, mild to moderate stickiness and messiness resulted. In mixtures including 40% SD alcohol 40 and either 5% propylene glycol or 15% propylene glycol, no stickiness and no messiness resulted. No skin irritation occurred in the test subjects, and no staining resulted from any of the mixtures. For a mixture which included 10% SD alcohol 40 and 9.2% propylene glycol, poor drying time was observed; and four of seven test subjects found the mixture to be better than their present deodorant or anti-perspirant. In the other mixtures including a higher percentage of SD alcohol 40, drying time was good; and twenty-one of the twenty-six test subjects found the mixture to be better than their present deodorant or anti-perspirant.

2) Foot deodorant—same results as 6(b) (1) above for underarm use.

Subjects

Twelve subjects tested the following concentration for both underarm and foot deodorant:
a) 5 gm/100 ml powdered crystal with 47.8% deionized water, 40% SD alcohol 40, 5% propylene glycol, 2% dimethicone copolyol phosphate, and 0.12% triclosan.

Seven subjects tested the following concentration:
a) 4.5 gm/100 ml powdered crystal with 75.13% deionized water, 10% SD alcohol 40, 9.2% propylene glycol, 1% dimethicone copolyol phosphate, and 0.17% triclosan.

Fourteen subjects tested the following concentration:
a) 4.5 gm/100 ml powdered crystal with 38.35% deionized water, 40% SD alcohol 40, 15% propylene glycol, 2% dimethicone copolyol phosphate, and 0.15% triclosan.

Therefore, a total of 66 tests were performed.

The last mentioned test of Example 6 appeared to be the most effective, with the odor control excellent in thirteen of the fourteen subjects. Drying time was good. There was no staining; and stickiness and messiness were none in most of the subjects and mild in two of the subjects. The results were comparable for both underarm use and foot deodorant use.

EXAMPLE 7

| COMPOSITION | RANGES |
| --- | --- |
| Powdered crystal | 4.5 gm/100 ml |
| Propylene glycol | 5% |
| Hexachlorophene | 2% |
| Absolute ethanol | 40% |
| Distilled water | 46% to 47.5% |
| Menthol | 1% to 2.5% |

Methodology

Powdered crystal was dissolved in distilled water, then filtered. In a separate reaction, propylene glycol was mixed with absolute ethanol and gently stirred. Hexachlorophene and menthol were then dissolved in the propylene glycol/absolute ethanol mixture, and that solution was added to the clear filtrate from the first reaction.

Results a) Chemical—no crystallization took place and the solution remained a clear liquid.
b) Clinical—foot deodorant/footwear deodorizer—mixtures containing 2% and 2.5% menthol provided excellent odor control by the sniff test in all of the test subjects. All subjects reported excellent coolness and a "fresh" feeling from these mixtures. In a mixture containing 1% menthol, odor control for both feet and footwear was considered good. The fresh feeling and coolness was judged fair to good by the test subjects.

Subjects

Ten subjects tested each of the following concentrations as a foot deodorant and a footwear deodorizer:
a) 4.5 gm/100 ml powdered crystal with 47.5% water, 5% propylene glycol, 5% absolute ethanol, 2% hexachlorophene, and 1% menthol.
b) 4.5 gm/100 ml powdered crystal with 46.5% water, 5% propylene glycol, 40% absolute ethanol, 2% hexachlorophene, and 2% menthol.
c) 4.5 gm/100 ml powdered crystal with 46% water, 5% propylene glycol, 40% absolute ethanol, 2% hexachlorophene, and 2.5% menthol.

Therefore, a total of 60 tests were performed. No test of this solution was made as an underarm deodorant.

EXAMPLE 8

| COMPOSITION | RANGES |
| --- | --- |
| Powdered crystal | 4.5 gm/100 ml |
| Hexachlorophene | 2% |
| Absolute ethanol | 40% |
| Distilled water | 48% to 49.5% |
| Menthol | 1% to 2.5% |

Methodology

Powdered crystal was dissolved in distilled water, then filtered. In a separate reaction, hexachlorophene and menthol were dissolved in the absolute ethanol, and that solution was then added to the clear filtrate from the first reaction.

Results a) Chemical—all mixtures resulted in a clear solution with no crystallization or flocculation.
b) Clinical
1) Foot deodorant/footwear deodorizer—mixtures containing 2% and 2.5% menthol were judged to be good to excellent control by the sniff test in all of the test subjects. All of the test subjects for these mixtures also reported good to excellent coolness and "fresh feeling" when the product was used as a foot deodorant. For a mixture containing 1% menthol, the odor control reported by all subjects was fair to good, as was the coolness and "fresh feeling". In all mixtures, eight of ten subjects reported excessive messiness when used as a foot deodorant.

Subjects

Ten subjects tested each of the following concentrations as a foot deodorant and a footwear deodorizer:
a) 4.5 gm/100 ml powdered crystal with 49.5% water, 40% absolute ethanol, 2% hexachlorophene, and 1% menthol.
b) 4.5 gm/100 ml powdered crystal with 48.5% water, 40% absolute ethanol, 2% hexachlorophene, and 2% menthol.
c) 4.5 gm/100 ml powdered crystal with 48% water, 40% absolute ethanol, 2% hexachlorophene, and 2.5% menthol.

Therefore, a total of 60 tests were performed. No test of this solution was made as an underarm deodorant.

EXAMPLE 9

| COMPOSITION | RANGES |
| --- | --- |
| Powdered crystal | 4.5 gm/100 ml |
| Propylene glycol | 5% |
| Dimethicone | 2% |
| SD alcohol 40 | 40% |
| Distilled water | 45.38% to 46.88% |
| Triclosan | .12% |
| Menthol | 1% to 2.5% |

Methodology

Powdered crystal was dissolved in distilled water, then filtered. In a separate reaction, propylene glycol was mixed with SD alcohol 40 and gently stirred. Dimethicone, triclosan and menthol were then dissolved in the propylene glycol/alcohol mixture, and that solution was then added to the clear filtrate from the first reaction.

Results a) Chemical—all of the above mixtures resulted in a clear liquid with no crystallization and no flocculation.

b) Clinical
  1) Foot deodorant/footwear deodorizer—all mixtures which contained between 1b menthol and 2.5% menthol with a corresponding reduction in the amount of water used produced good to excellent odor control, when the product was used as a foot deodorant and a footwear deodorizer. In all cases, in all subjects, coolness and "fresh feeling" were judged to be excellent.

Subjects

Ten subjects tested each of the following concentrations as a foot deodorant and as a footwear deodorizer:

a) 4.5 gm/100 ml powdered crystal with 46.88% water, 40% SD alcohol 40, 5% propylene glycol, 2% dimethicone, 1% menthol and 0.12% triclosan.

b) 4.5 gm/100 ml powdered crystal with 45.88% water, 40% SD alcohol 40, 5% propylene glycol, 2% dimethicone, 2% menthol and 0.12% triclosan.

c) 4.5 gm/100 ml powdered crystal with 45.38% water, 40% SD alcohol 40, 5% propylene glycol, 2% dimethicone, 2.5% menthol and 0.12% triclosan.

Therefore, a total of 60 tests were performed.

In the compositions of Examples 6 and 9, the alcohol used was SD alcohol 40, which is a special denatured alcohol used in the cosmetics industry, and it is commercially identified by this designation. The triclosan used in various ones of the foregoing examples is a bactericide, which enhanced the duration of the odor control produced by the product.

The composition of Example 1 (where the liquid carrier is one hundred percent distilled water) was found to be the only solution of the different examples which is believed suitable for perineal area odor control. Some irritation was experienced by some subjects when the compositions in Examples 2, 3, 4 and 5 were used in the perineal area.

From the foregoing, the range of powdered crystal which is dissolved in each 100 ml liquid typically extended from 2.5 gm/100 ml to 7 gm/100 ml (with the exception of Example 1, which went as high as 14 gm/100 ml). As is apparent from the listed clinical results, the most effective odor control appears to be obtained when the powdered crystal is equal to or greater than 4.5 gm/100 ml of liquid, with over 40% ethanol or SD alcohol 40 and under 5% propylene glycol.

In addition to providing good deodorant odor control, particularly for feet and underarm areas, the liquid crystal deodorant, which is described above in the various examples, also functions as a natural bactericide. The crystal dissolves into a true solution in all of the different compositions which have been discussed above. Application may be made by means of pump spray, aerosol or roll-on, as desired.

Other uses, besides personal body deodorant, for the products of the above examples are for a shoe deodorizer, pet deodorant, pet litter box deodorant, and others.

Various changes and modifications to the invention, which has been described above, will occur to those skilled in the art without departing from the true scope of the invention as defined in the appended claims.

We claim:

1. A liquid crystal deodorant including in combination:
   powdered crystalline double sulfate of aluminum selected from the group consisting of potassium aluminum sulfate and ammonium aluminum sulfate dissolved in a saturated solution comprising between 2.5 grams and 7.0 grams of crystalline double sulfate of aluminum per 100 milliliters of liquid, said liquid consisting of between thirty-five percent and eighty percent of distilled water, between five percent and fifteen percent propylene glycol and forty percent to fifty percent of denatured alcohol, one percent to two percent dimethicone copolyol phosphate, and 0.12 percent to 2 percent of a bactericide selected from the group of triclosan and hexachlorophene.

2. The combination according to claim 1 wherein said denatured alcohol is SD alcohol 40.

3. The combination according to claim 1 wherein said bactericide comprises less than one percent by volume of triclosan.

4. The combination according to claim 3 wherein said powdered crystalline double sulfate of aluminum comprises potassium aluminum sulfate.

* * * * *